(12) United States Patent
Khalili (10) Patent No.: US 7,815,679 B2
(45) Date of Patent: Oct. 19, 2010

(54) MODULAR MOTION PRESERVATION ARTIFICIAL SPINAL JOINT ASSEMBLY

(75) Inventor: Farid Bruce Khalili, Briar Cliff Manor, NY (US)

(73) Assignee: Cardo Medical, Inc., Beverly Hills, CA (US)

( * ) Notice: Subject to any disclaimer, the term of this patent is extended or adjusted under 35 U.S.C. 154(b) by 930 days.

(21) Appl. No.: 10/696,846

(22) Filed: Oct. 31, 2003

(65) Prior Publication Data

US 2004/0172021 A1   Sep. 2, 2004

Related U.S. Application Data

(60) Provisional application No. 60/437,878, filed on Jan. 6, 2003, provisional application No. 60/476,643, filed on Jun. 9, 2003.

(51) Int. Cl.
*A61F 2/44* (2006.01)
(52) U.S. Cl. ............................ 623/17.15; 623/17.11
(58) Field of Classification Search ... 623/17.11–17.16, 623/20.22; 606/246–249, 297
See application file for complete search history.

(56) References Cited

U.S. PATENT DOCUMENTS

| | | | | |
|---|---|---|---|---|
| 4,759,766 A | * | 7/1988 | Buettner-Janz et al. | 623/17.15 |
| 5,425,773 A | * | 6/1995 | Boyd et al. | 623/17.15 |
| 5,885,287 A | * | 3/1999 | Bagby | 623/17.16 |
| 6,113,638 A | * | 9/2000 | Williams et al. | 606/246 |
| 6,120,503 A | * | 9/2000 | Michelson | 606/297 |
| 6,454,806 B1 | * | 9/2002 | Cohen et al. | 623/17.15 |
| 6,669,732 B2 | * | 12/2003 | Serhan et al. | 623/17.16 |
| 6,989,032 B2 | * | 1/2006 | Errico et al. | 623/17.14 |
| 2001/0032017 A1 | * | 10/2001 | Alfaro et al. | 623/17.11 |
| 2004/0133281 A1 | * | 7/2004 | Khandkar et al. | 623/17.15 |
| 2004/0143332 A1 | * | 7/2004 | Krueger et al. | 623/17.14 |

FOREIGN PATENT DOCUMENTS

| | | | |
|---|---|---|---|
| EP | 1344508 A1 | * | 9/2003 |
| WO | WO 9404100 A1 | * | 3/1994 |
| WO | WO 0013619 A1 | * | 3/2000 |

OTHER PUBLICATIONS

Translation of WO 94/04100 to Mazda.*

* cited by examiner

*Primary Examiner*—Brian E. Pellegrino
(74) *Attorney, Agent, or Firm*—Matthew B. Denier, Esq.; Gibson & Dernier LLP (57) ABSTRACT

A system of reconstruction for a spinal joint allows adjacent vertebrae to move relative to each other in a generally pivotal manner and in a limited sliding manner in either or both of the anterior-posterior direction and the medial-lateral direction. The system includes base components and a middle component. The base components are for attachment to adjacent vertebrae and support a pivoting cooperative engagement of a concave or cup-shaped component with a convex or dome-shaped component.

12 Claims, 7 Drawing Sheets

MODULAR MOTION PRESERVATION ARTIFICIAL SPINAL JOINT ASSEMBLY

RELATED APPLICATIONS

This application is related to provisional application 60/437,878 filed Jan. 6, 2003 and 60/476,643 filed Jun. 9, 2003, incorporating the same by reference and claiming priority therefrom.

TECHNICAL FIELD

The present invention relates to implantable artificial joint assemblies and, more particularly, to a modular joint assembly that allows a predetermined amount of desired motion to a joint and that is particularly well suited for use in reconstructing a spinal disc section of a spine.

BACKGROUND OF THE INVENTION

In orthopedics it is known to use various types of reconstruction assemblies to repair bone joints that have become deteriorated, damaged or degenerative, such as due to trauma or disease. Some reconstructions involve the use of various components such as bone screws, plates, bone grafts, fusion implants and other components. Depending on the type and method of reconstruction selected, complete stabilization with no movement may be selected, or a predetermined amount of controlled movement may be selected. In one technique of spinal reconstruction, for example, fusion of adjacent vertebrae is achieved using one or more plates fastened to adjacent vertebral segments in order to join the vertebral segments in a predetermined relationship for stabilization, sometimes installing a fusion device such as an implant or bone graft.

While complete fusion and, thus, resultant loss of movement between adjacent vertebrae is sometimes prescribed, fusion does limit movement and in the long term may adversely affect vertebrae adjacent to the fused joint by imposing heightened stress and wear. An alternative to fusion using motion preservation devices restores significant motion and disc space height which minimizes stress concentrations and pain.

The various known systems for allowing controlled movement of joint reconstructions have shortcomings. Such shortcomings include lack of versatility so as to require multiple configurations and sizes of hardware on hand during surgery; prohibitively complex or expensive components; lack of anatomical correspondence with resultant poor fit, high stress concentrations and unnatural load forces on adjacent or fused bone segments; and other shortcomings. Known motion preservation devices are generally restricted to only very stable constructs and degenerative disc disease cases, which is only 5%-10% of all cases.

One known device involves a first, or upper, component; a second, or lower, component; and a middle component. The upper and lower components are generally similar and each includes a base portion adapted to be fixed to an end-face of one of two adjacent vertebrae. Each of the upper and lower components further includes a cup portion formed by an axially extending annular wall having generally concentrically contained therein a generally concave surface. The middle component comprises upper and lower portions that are convex and, preferably, a middle circumferential flange. The upper and lower convex portions are adapted to be matingly received in the respective concave portions when the middle component is positioned between the upper and lower components. The middle component, thus, can slide relative to the upper and lower components due to the relative movement of the convex portions against the concave portions. The middle flange limits movement when it engages the respective annular walls. Varying the shape and/or size of the flange will resultantly vary the amount of allowable pivot. The movement described allows adjacent vertebrae to move relative to each other in a generally pivotal manner at two points of movement. If desired, the annular wall of one or both of the cup portions may be of varying height along its circumference, so the when the system is fully assembled, the attached vertebrae are held in a relatively angled relationship intended to reproduce naturally occurring lordotic orientations.

OBJECTS OF THE INVENTION

It is an object of the present invention to provide a joint reconstruction system that overcomes the above-mentioned shortcomings and that achieves additional, inherent objectives apparent from the description set forth below.

It is a further object of the present invention to provide a joint reconstruction system particularly well-suited, as described with respect to the preferred embodiments, for spinal reconstruction. These and other objects are described below or inherent with respect to the present invention.

SUMMARY OF THE INVENTION

The present invention is described in the preferred embodiments as directed to a system of reconstruction for a spinal joint. It is understood, however, that the present invention is not limited to spinal reconstruction and, as understood by one skilled in the art, may be adapted for application to other types of joints.

In the preferred embodiments allowing adjacent vertebrae to move relative to each other in a generally pivotal manner and, in one of the embodiments, in a limited sliding manner in either or both of the anterior-posterior direction and the medial-lateral direction, a system of reconstruction of a spinal joint includes base components and a middle component. The base components are for attachment to adjacent vertebrae and support a pivoting cooperative engagement of a concave or cup-shaped component with a convex or dome-shaped component.

In both embodiments, the base components are adapted for use with any one of a variety of middle components of a selected size, shape, or angle for a desired range and angle of pivot, a desired height or spacing, and a desired amount of sliding movement. These embodiments are described below.

DESCRIPTION OF THE PREFERRED EMBODIMENTS

Figure 1:
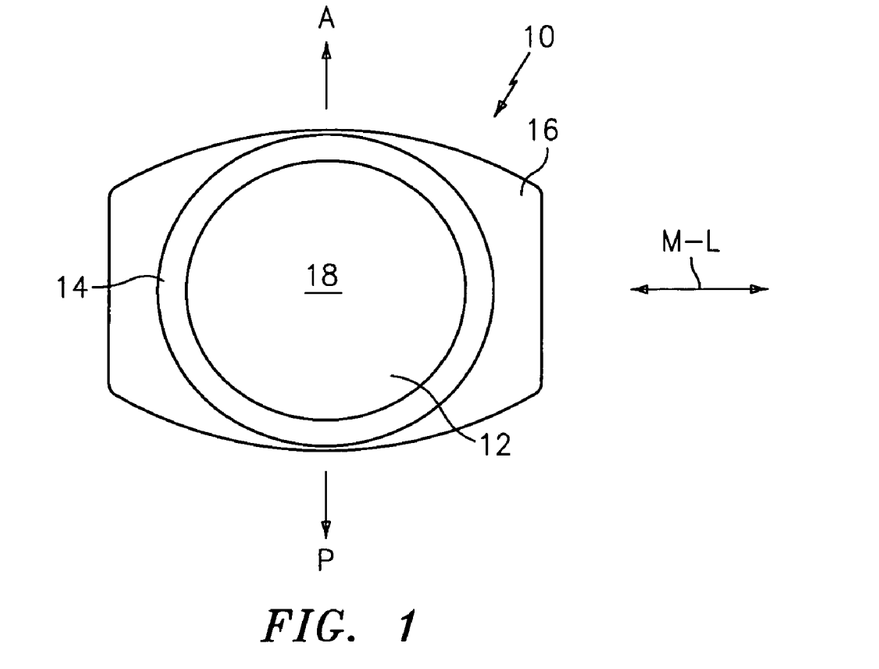
FIG. 1 is an image of a bottom side of a superior base component of a first embodiment of the present invention.
Figure 2:
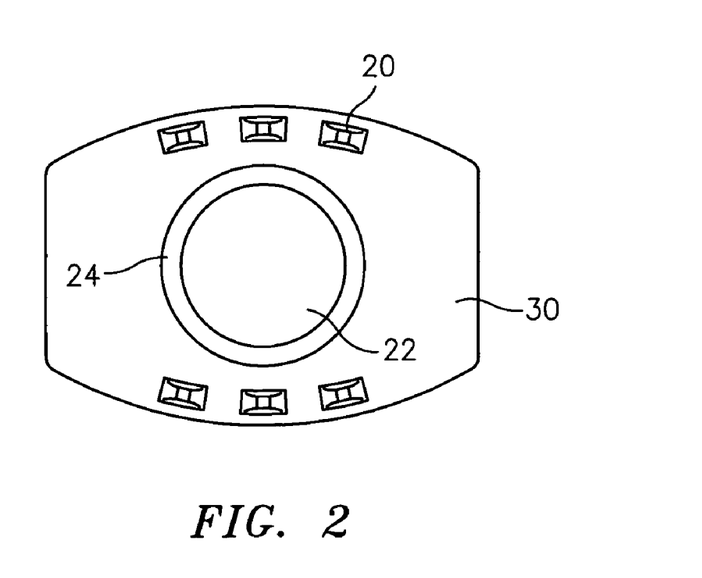
FIG. 2 is an image of a top side of an superior base component of a first embodiment of the present invention.

A first embodiment assembly according to the present invention is described with respect to FIGS. 1-7 and 15. A superior base component (10), as shown in FIGS. 1-2, has a anterior and posterior sides identified by the letters "A" and "P", respectively. As shown in FIG. 1, a circular concave portion (12) on the bottom side of the superior base component (10) has an outer rim (14) that is raised from the plate section (16) outside of the concave portion (12). The center (18) of the concave portion (12) is lower than the rim (14). The top side of the superior base component (10), as shown in FIG. 2, has a plurality of sharpened teeth (20) extending therefrom, and a pair of concentric, raised circular portions (22, 24). Referring to the side view of FIG. 15, the raised circular portions (22, 24) have angled walls (26, 28), respectively, that taper in the direction toward the plate section (30). This enable bone growth from the surrounding bone tissue (32) to anchor or secure the superior base component (10) to a vertebra while in use.

Figure 3:
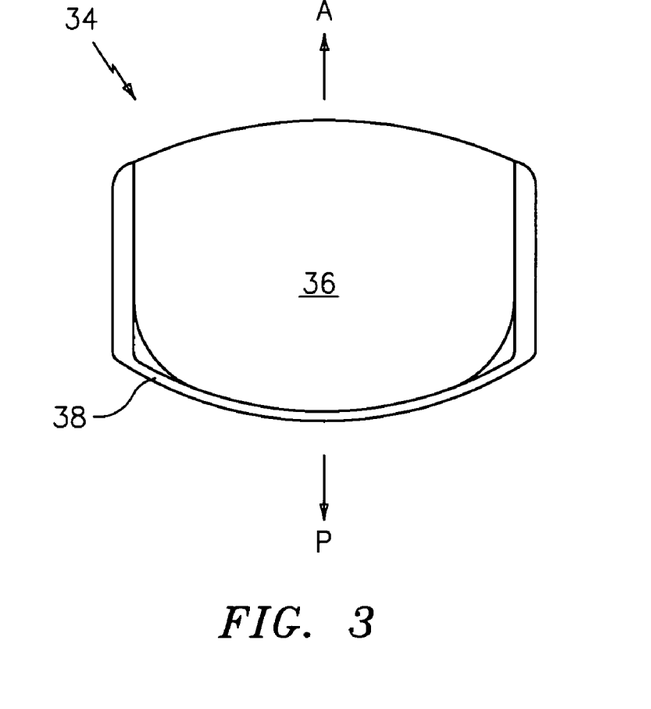
FIG. 3 is an image of a top side of an inferior base component of a first embodiment of the present invention.
Figure 4:
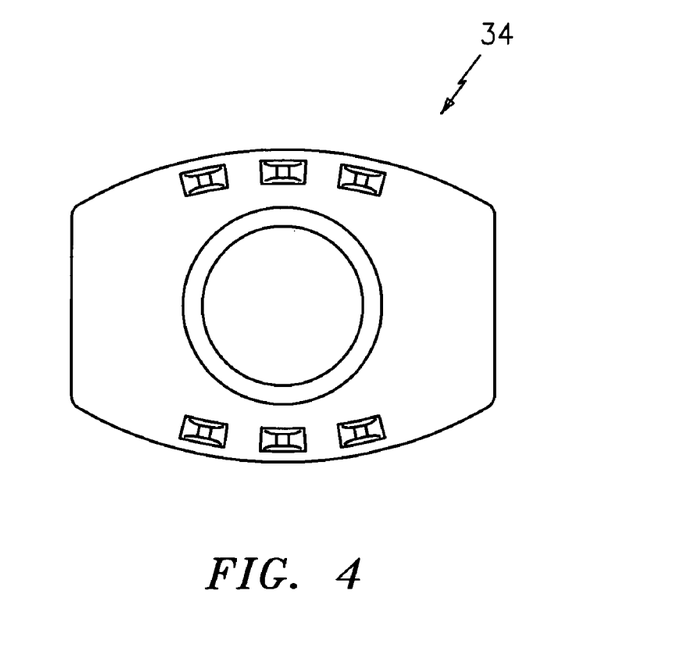
FIG. 4 is an image of a bottom side of an inferior base component of a first embodiment of the present invention.
Figure 5:
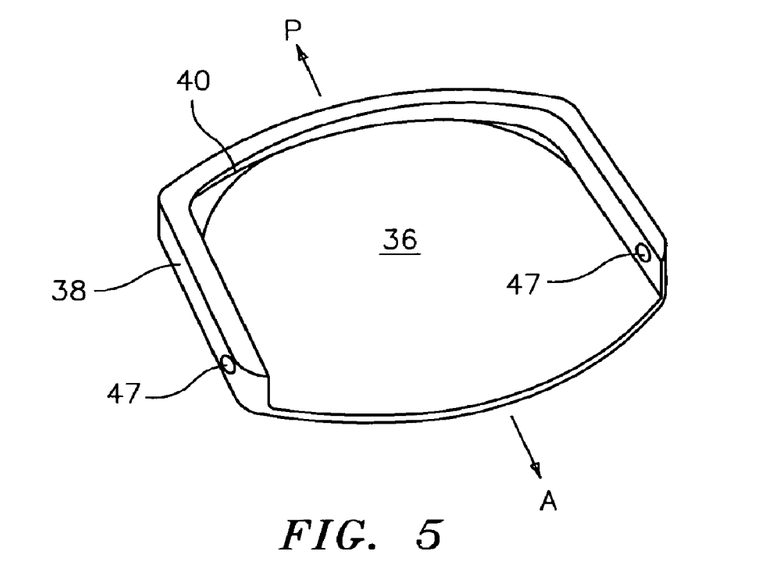
FIG. 5 is an image of a top, perspective view of an inferior base component of a first embodiment of the present invention.

An inferior base component (34) is shown in FIG. 3, and the top side has a plate portion (36) and three sides of raised wall (38) along three outer edges. The bottom side of the inferior base component (34), as shown in FIG. 4, is substantially identical to the top side of the superior base component (10) in form and function. Referring to FIG. 5, it can be seen that the top side of the inferior base component (34) has a slot (40) running along the inside surface of the raised wall (38).

Figure 6:
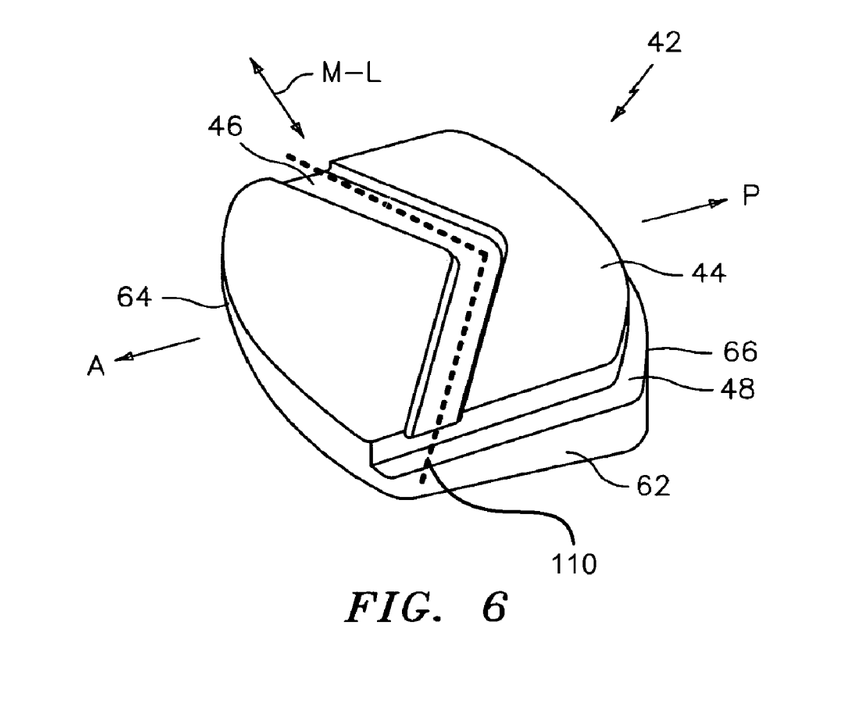
FIG. 6 is an image of a bottom side of a middle component of a first embodiment of the present invention.
Figure 7:
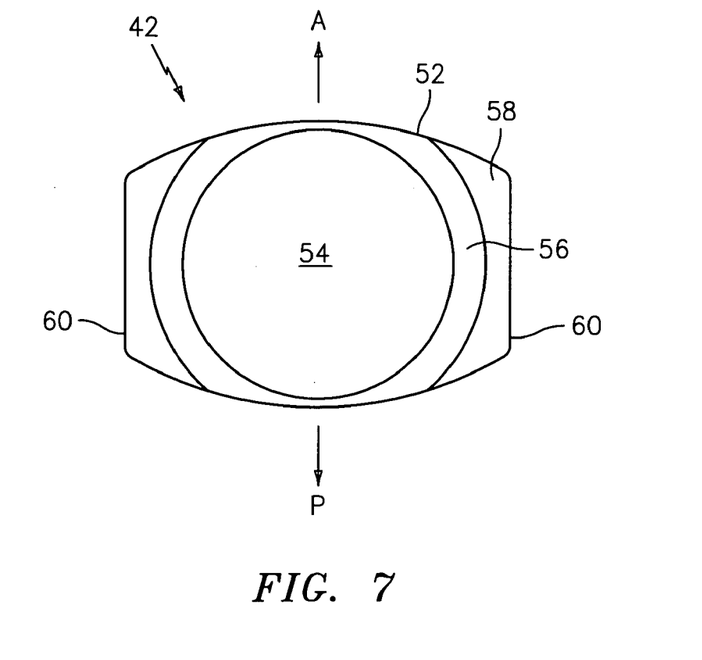
FIG. 7 is an image of a top side of a middle component of a first embodiment of the present invention.

As shown in FIG. 6, a middle component (42) of the first embodiment has a bottom side (44) that includes a spring-retention groove (46), and a side slot (48) around three sides of the sidewall (50) of the middle component. The spring-retention groove (46) enables a spring clip (110) to be positioned therein with ends of the spring clip expanding outwardly from the groove (46) in the medial-lateral (M-L) direction to engage the holes (47) for positive locking. The top side (52) of the middle component (42), as shown in FIG. 7, has a convex or raised dome portion (54) that has a circumferential groove (56) and raised wing surfaces (58) that taper downward toward the outside edges (60).

In use, the inferior base component (34) is positioned in a space above a first vertebrae (not shown) where vertebral disc material has been moved. The inferior base component (34) is placed into contact with the first vertebrae whereby the teeth on the bottom surface bite into the bone surface of the vertebrae. The middle component (42) is selected from among a variety of available such components of varying height, angle, and/or convex shape depending on the anatomical or medical conditions, and is slid into the slot (40) of the inferior component (34) via the contours formed by the slot (48). For example, as shown in FIG. 6, the side wall (62) varies between the anterior side (64) and the posterior side (66) in accordance with desired angles to accommodate natural lordosis. This angle can be increased, decreased, or reversed to accommodate any desired angle such that the same components can be used for lumbar or cervical applications.

Next, the superior component (10) is positioned such that its teeth (20) bite into the bone surface of a second vertebrae, with the concave portion (12) engaging the convex portion (54) of the middle component (42). The contact area between the concave portion (12) and the convex portion (54) is the load-supporting area between the adjacent vertebrae, and it facilitates relative rotations between the adjacent vertebrae in a ball-and-socket manner. Over-rotation is prevented by the contact of the rim (14) and the circumferential groove (56). Additional support against over-rotation is provided by the body's natural ligament tension, or the use of supplemental tension forces between the adjacent vertebrae attributable to artificial ligament devices such as cords or mesh.

Figure 8:
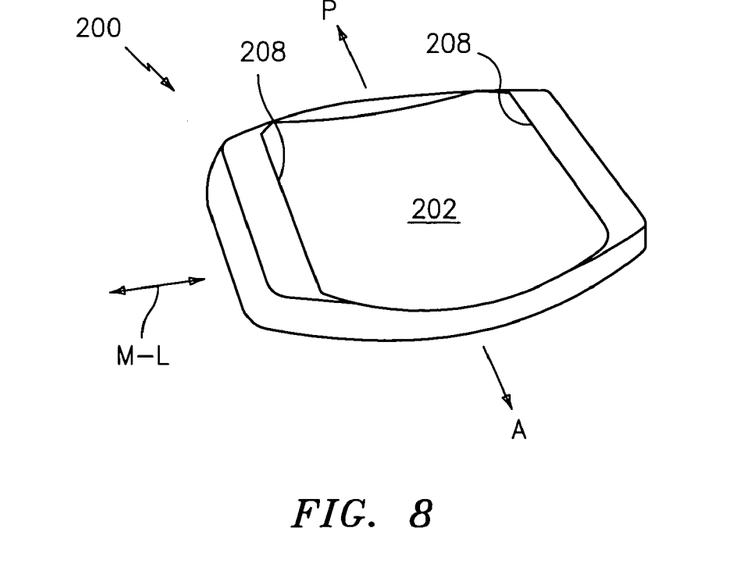
FIG. 8 is an image of a top side of an inferior base component of a second embodiment of the present invention.
Figure 9:
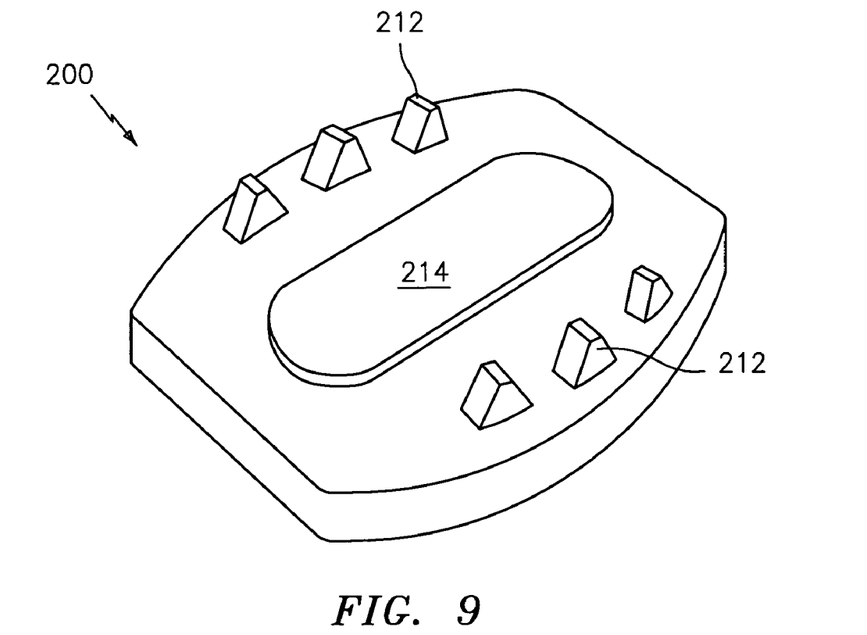
FIG. 9 is an image of a bottom side of an inferior base component of a second embodiment of the present invention.
Figure 10:
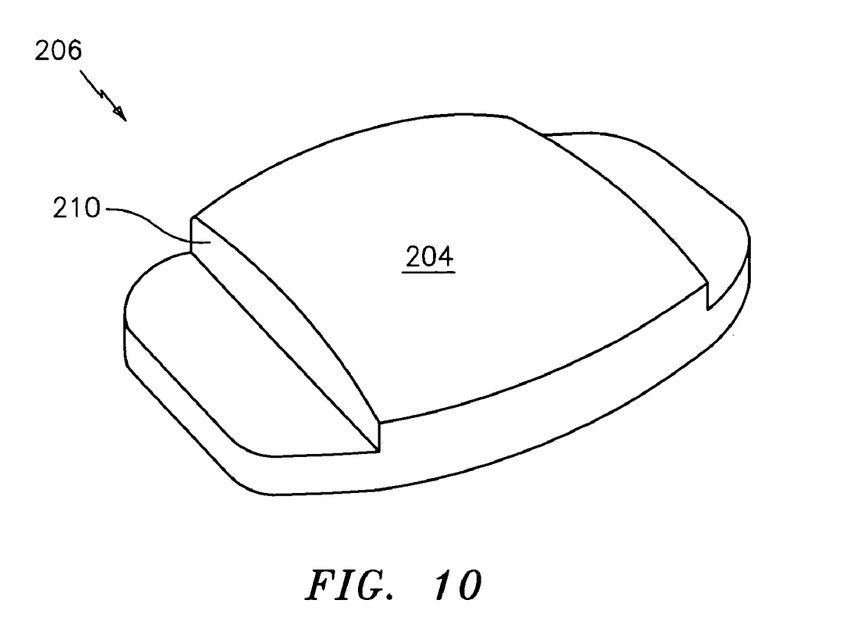
FIG. 10 is an image of a bottom side of a middle component of a second embodiment of the present invention.

A second embodiment of the present invention is illustrated in the assembly shown in FIGS. 8-13. Referring to FIG. 8, the inferior base component (200) has a central portion (202) that is generally convex, but that has varying radii along the anterior-posterior direction and along the medial-lateral direction. Optionally, the radii can be made to vary in only one of the above-mentioned directions or in neither. The advantage of using the varying radii in this manner allows for relative sliding between the central portion (202) and the domed or convex portion (204) of the bottom side of the middle component (206), shown in FIG. 10, in addition to rotation. The central portion (202) has sidewalls (208) that engage the sidewalls (210) of the convex portion (204) of the middle component (206) to block or prevent over-rotation and over-sliding. The bottom side of the inferior base component (200), shown in FIG. 9, has sharp teeth (212) that bite into the upper surface of a first vertebrae. The bottom side may be provide with raised portions (214) having angled sidewalls that cooperate with bone in-growth for enhanced anchoring.

Figure 11:
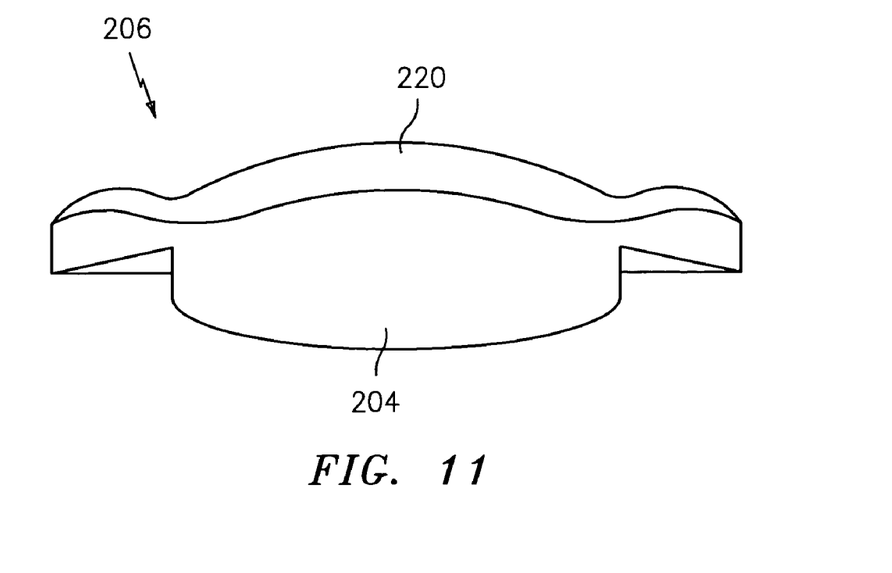
FIG. 11 is an image of a side view of a middle component of a second embodiment of the present invention.
Figure 12:
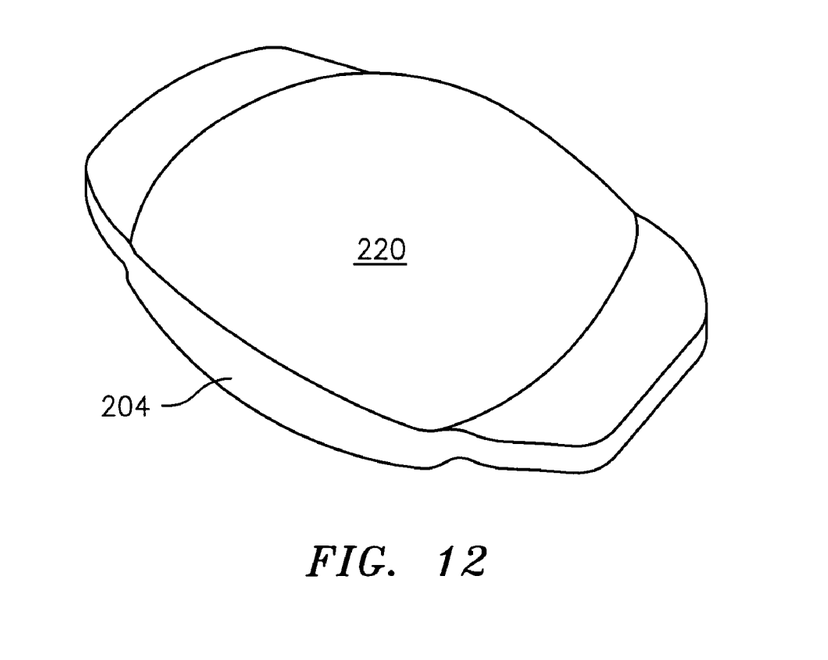
FIG. 12 is an image of a top side of a middle component of a second embodiment of the present invention.
Figure 13:
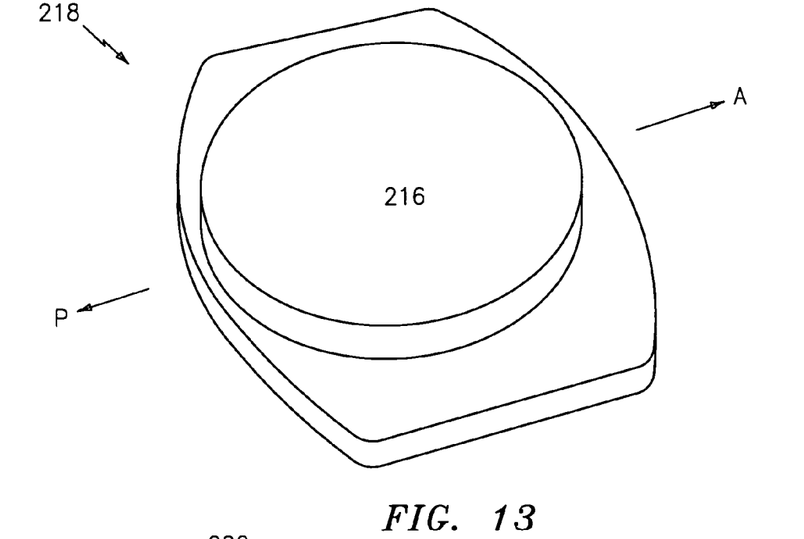
FIG. 13 is an image of a bottom side of a superior base component of a second embodiment of the present invention.
Figure 14:
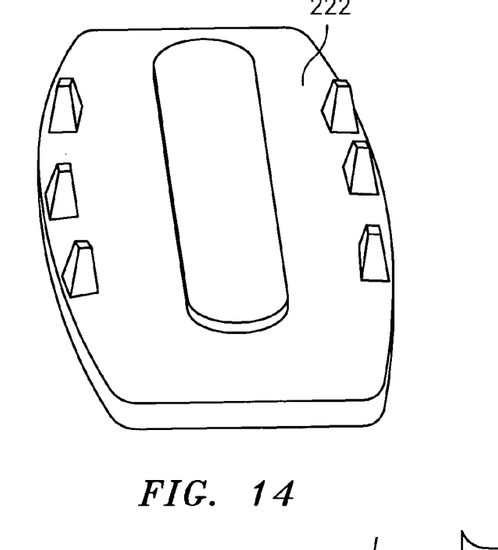
FIG. 14 is an image of a top side of a superior base component of a second embodiment of the present invention.
Figure 15:
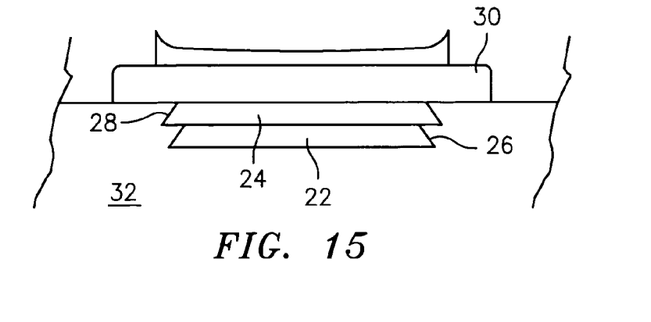
FIG. 15 is a side, cross-sectional view of the superior base component of the first embodiment of the present invention.

The upper side of the middle component (206), as shown in FIGS. 11-12, is dome or convex shaped (220) to engage a concave portion (216) of a bottom side of superior base component (218) shown in FIG. 13. The concave portion (216) is of constant radius or it may have a flattened central portion within so that the only motion between the concave portion (216) and the convex portion (220) of the middle component (206) is rotational, and does not include sliding movement. A flattened middle portion in the concave section increases the range of rotation over a purely concave section. The concave portion (216) may be off-set relative to the center of the component, as shown, so that its center or rotation reflects the naturally anatomically occurring center of rotation between the adjacent vertebrae between which the assembly is constructed. In this case, the center of the concave portion (216) is closer to the posterior side. The upper side (222) of the superior base component (218) is substantially similar to the lower side of the inferior base component (FIG. 9) in form and function.

As shown in FIGS. 16-17, by way of example, the various dimensions of the components, in this case the superior component (218), may be varied according to anatomical and other parameters.

Thus, in use, when the inferior, middle and superior components (200, 206, 218) are assembled in tension from either the body's natural ligaments or with enhanced artificial ligament type devices, the relative movement between the superior and middle components is limited to rotation, and the relative movement between the middle and inferior components includes rotation and sliding.

The components described herein with respect to the preferred embodiments may be made from suitable materials including, but not limited to, titanium, cobalt chromium moly, polyethylene, and implantable stainless steel.

While the preferred embodiments of the present invention has been described herein, various modification may be made without departing from the scope of the invention.

What is claimed:

1. A prosthetic assembly for use between a pair of adjacent vertebrae, comprising:
   a first base component having a first side adapted for engaging the first of the adjacent vertebrae, and an opposing second side comprising a concave portion;
   a second base component having a first side adapted for engaging the second of the adjacent vertebrae, and an opposing second side;
   the first sides of each of the base components comprising a plurality of sharpened teeth and a raised portion comprising a pair of concentric raised circular portions stacked, one atop the other, each of the raised portions having angled sidewalls that taper inwardly in the direction towards the base component to cooperate with bone in-growth, as the vertebra-engaging adaptation; and
   a middle component having a first side with a convex portion thereon adapted to engage the concave portion of the first base component, and an opposing second side;
   wherein the second base component and the middle component each comprises a slot having edges extending linearly from an anterior edge to a posterior edge of each respective component such that the second side of the second base component slideably receives the second side of the middle component and the middle component includes at least one raised wing surface that tapers downwardly toward at least one outside edge of the middle component.

2. The assembly according to claim 1, wherein:
   said concave portion has a constant radius.

3. The assembly according to claim 1, wherein:
   said convex portion extends above a generally flat surface and is surrounded by a groove that extends below said generally flat surface.

4. The assembly according to claim 1, wherein said convex portion has a center of radius that is closer to said anterior edge than it is to said posterior edge.

5. The assembly according to claim 1, wherein:
   the middle component varies in height along a direction between the anterior edge and the posterior edge.

6. The prosthetic assembly of claim 1, wherein:
   the sharpened teeth are positioned near a periphery of the first side of the base component and the raised portion with angled sidewalls is positioned in a central area thereof.

7. The prosthetic assembly of claim 1, wherein the one raised portion that is atop the other raised portion has a flat surface.

8. The prosthetic assembly of claim 1, wherein the second base component further includes a raised wall disposed on the second side thereof such that the raised wall comprises the slot that slidingly receives the second side of the middle component.

9. The prosthetic assembly of claim 8, wherein the raised wall includes one or more apertures operating to engage a clipping element disposed on the second side of the middle component such that the second side of the middle component is attached to the second side of the second base component.

10. The prosthetic assembly of claim 9, wherein the clipping element is disposed in a groove on the second side of the middle component, and at least one portion of the clipping element engages the one or more apertures of the raised wall.

11. The prosthetic assembly of claim 1, wherein the middle component includes a circumferential groove that operates to mate with an outer rim disposed on and/or around the concave portion of the second side of the first base component such that over-rotation is reduced and/or prevented.

12. The prosthetic assembly of claim 1, wherein the opposing second side of the middle component further comprises a spring retention groove extending across a length of the middle component configured to receive a clipping element.

* * * * *